US010702324B2

(12) United States Patent
Marek et al.

(10) Patent No.: US 10,702,324 B2
(45) Date of Patent: Jul. 7, 2020

(54) REDUCTION TOOL

(71) Applicant: OsteoMed LLC, Addison, TX (US)

(72) Inventors: Matthew Geoffrey Marek, Plano, TX (US); Viorel Mocanu, Lewisville, TX (US); Ronald Litke, Sandy Hook, CT (US); Spencer Shore, Hamden, CT (US); Scott Reed, Winchester, CT (US)

(73) Assignee: OsteoMed LLC, Addison, TX (US)

( * ) Notice: Subject to any disclaimer, the term of this patent is extended or adjusted under 35 U.S.C. 154(b) by 640 days.

(21) Appl. No.: 15/444,028

(22) Filed: Feb. 27, 2017

(65) Prior Publication Data

US 2018/0243022 A1 Aug. 30, 2018

(51) Int. Cl.
*A61B 17/86* (2006.01)
*A61B 17/88* (2006.01)

(52) U.S. Cl.
CPC ........ *A61B 17/8891* (2013.01); *A61B 17/862* (2013.01); *A61B 17/863* (2013.01)

(58) Field of Classification Search
CPC . A61B 17/864; A61B 17/8645; A61B 17/888; A61B 17/8891
See application file for complete search history.

(56) References Cited

U.S. PATENT DOCUMENTS

| | | | |
|---|---|---|---|
| 4,175,555 A * | 11/1979 | Herbert | A61B 17/863 606/304 |
| 4,988,351 A | 1/1991 | Paulos et al. | |
| 5,409,490 A * | 4/1995 | Ethridge | A61B 17/8605 606/80 |
| 5,797,912 A | 8/1998 | Runciman et al. | |
| 5,899,906 A | 5/1999 | Schenk | |
| 6,048,344 A | 4/2000 | Schenk | |
| 6,415,693 B1 * | 7/2002 | Simon | A61B 17/8891 81/453 |
| 6,984,235 B2 | 1/2006 | Huebner | |
| 8,070,786 B2 | 12/2011 | Huebner et al. | |
| 8,216,243 B2 | 7/2012 | Yevmenenko et al. | |
| 8,273,113 B2 | 9/2012 | Frenk et al. | |
| 8,540,726 B2 | 9/2013 | Yevmenenko et al. | |
| 8,721,694 B2 | 5/2014 | Patterson et al. | |
| 9,011,505 B2 | 4/2015 | Prandi et al. | |
| 9,113,976 B2 | 8/2015 | Yevmenenko et al. | |
| 2008/0234763 A1 | 9/2008 | Patterson et al. | |
| 2013/0304032 A1 * | 11/2013 | Sardesai | A61B 17/864 604/522 |

* cited by examiner

*Primary Examiner* — Anu Ramana
(74) *Attorney, Agent, or Firm* — Norton Rose Fulbright US LLP

(57) ABSTRACT

Systems, tools, and screws for reducing a bone fracture are disclosed. In embodiments, the system comprises: a screw, a driver, a sleeve comprising a longitudinal bore configured to enable insertion of the driver through the sleeve, a locking mechanism configurable into a first state that locks the sleeve to the driver and a second state that unlocks the sleeve from the driver, and a retaining sleeve coupled to a first end of the driver and configured to couple to the screw. In the first state, the sleeve applies a compressive force while distal threads of the screw are driven into the bone while retaining proximal threads of the screw in the sleeve. After a desired compression is achieved, the locking mechanism is configured to the second state, allowing the proximal threads of the screw to be driven into the bone while maintaining application of the compressive force to the bone.

18 Claims, 9 Drawing Sheets

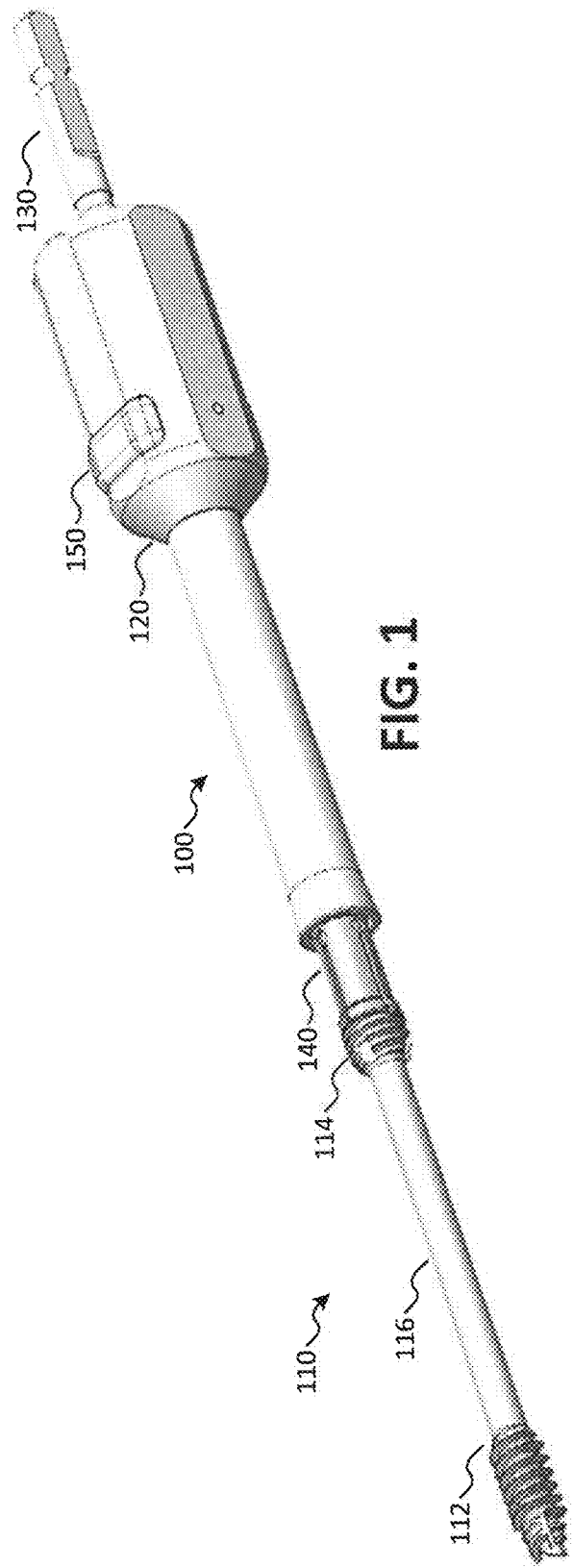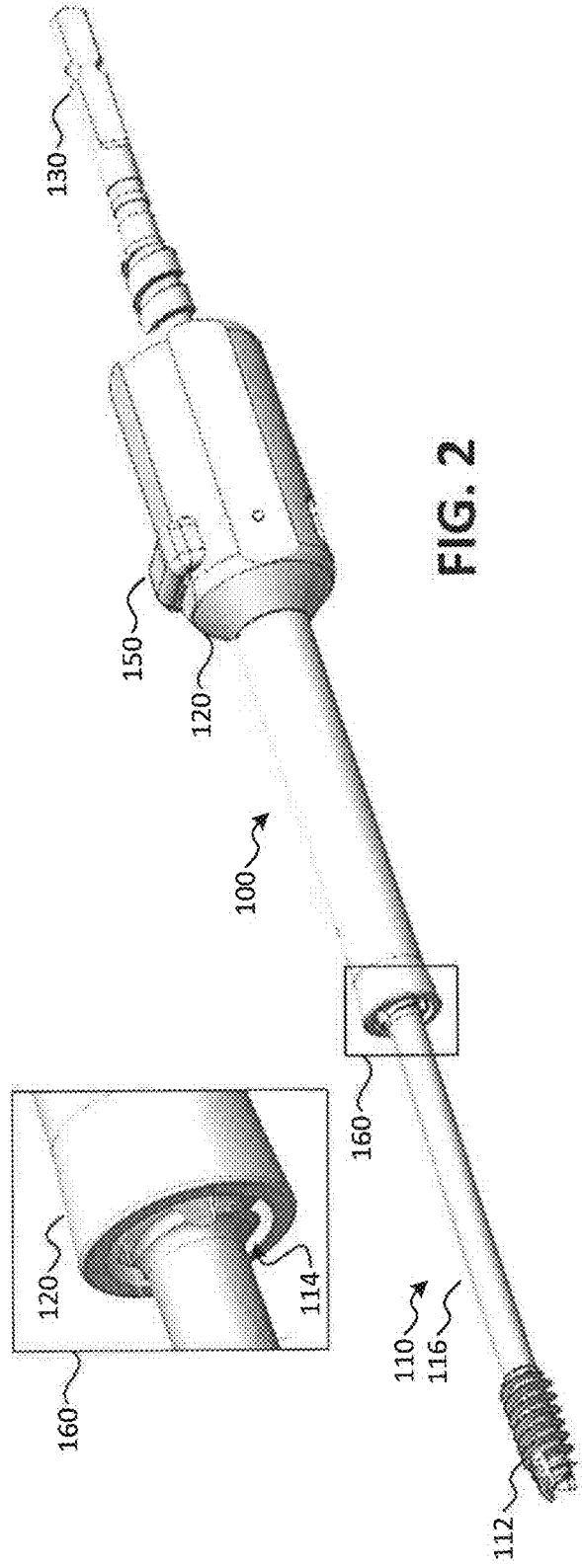

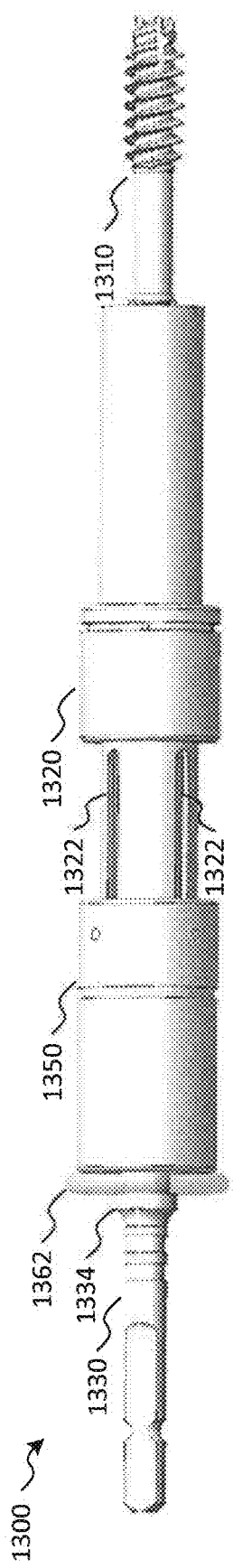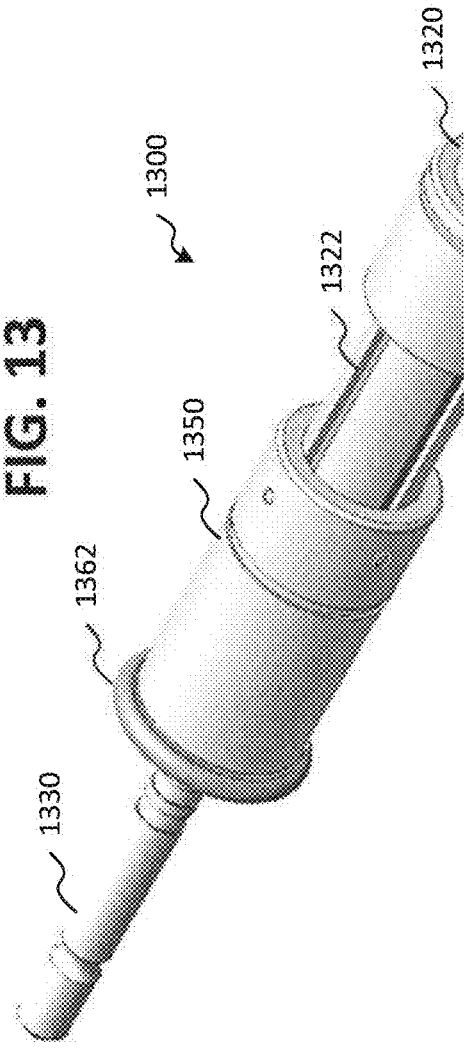
FIG. 13
FIG. 14

REDUCTION TOOL

TECHNICAL FIELD

The present application generally relates to systems, methods, and tools for reducing a bone fracture, and more particularly to systems, methods, and tools for providing improved compression during reduction of a bone fracture.

BACKGROUND

A bone fracture may result in two fragments or sections of bone becoming separated from one another, and screws may be used to fixate the bone fragments in proper alignment while the bone fragments heal. As the screws are driven into the bone, the fragments or sections may be drawn together, creating compression of the bone fragments, which may promote faster healing of the bone. However, it is not always easy to achieve a desired amount of compression during fixation of bone fragments. One technique for providing fixation and compression of these types of fractures involves driving one or more headed screws through the bone fragments. As the screw is driven into the bone, the head of the screw applies a force that draws the bone fragments together until a desired amount of compression is achieved. However, this technique is not always desirable because the head of the screw protrudes from the bone and may cause discomfort to, or damage, tissues surrounding the bone fracture. Using headless screws overcomes the drawbacks associated with headed screws, but presents other challenges with respect to achieving the desired amount of compression. For example, it may be difficult to maintain the appropriate amount of compression during reduction of a bone fracture using headless screws (e.g., because there is no head on the screw to apply a compressive force to the bone fragments and draw the bone fragments together).

BRIEF SUMMARY

The present disclosure describes systems, methods, tools, and screws for reducing a bone fracture. In embodiments, a system for reducing a bone fracture may include: a screw, a driver, a sleeve comprising a longitudinal bore configured to enable insertion of the driver through the sleeve, a locking mechanism configurable into a first state that locks the sleeve to the driver and a second state that unlocks the sleeve from the driver, and a retaining sleeve coupled to a first end of the driver and configured to couple to the screw. In the first state, the sleeve applies a compressive force as distal threads of the screw are driven into the bone. Additionally, in the first state, proximal threads of the screw are retained within the sleeve to prevent engagement with the bone, which may improve the amount of compression achieved during reduction of the fracture. After a desired compression is achieved, the locking mechanism may be configured to the second state, thereby unlocking the sleeve from the driver and allowing the proximal threads of the screw to be driven into the bone while maintaining application of the compressive force to the bone.

In another embodiment, a system for reducing a bone fracture may include: a screw, a driver configured to drive the screw into a bone, an inner sleeve comprising a longitudinal bore configured to enable insertion of the driver through the inner sleeve, an outer sleeve comprising a longitudinal bore configured to enable the inner sleeve and driver to be inserted through the outer sleeve, and a locking sleeve comprising a longitudinal bore configured to enable insertion of the outer sleeve through the locking sleeve. The locking sleeve may be configurable into a first state that locks the locking sleeve to the outer sleeve and prevents the retaining sleeve from exiting the outer sleeve, and a second state that unlocks the outer sleeve from locking sleeve and enables the retaining sleeve to exit the outer sleeve. The driver may include an inner sleeve interface configured to apply a force to the inner sleeve as the screw is driven into the bone. When the locking sleeve is configured into the first state, the force applied to the inner sleeve may be transferred to the bone through the locking sleeve and the outer sleeve. Additionally, in the first state, proximal threads of the screw are retained within the inner sleeve to prevent engagement with the bone, which may improve the amount of compression achieved during reduction of the fracture. After a desired compression is achieved, the locking sleeve may be configured to the second state, thereby unlocking the outer sleeve from the locking sleeve and allowing the proximal threads of the screw to be driven into the bone while maintaining application of the compressive force to the bone.

In embodiments, a screw may include a first threaded portion, a second threaded portion, and a non-threaded portion separating the first threaded portion and the second threaded portion. The first threaded portion may correspond to a first end of the screw (e.g., a tip or leading end of the screw) and the second threaded portion corresponding to a second end of the screw (e.g., a tail or trailing end of the screw). The second end of the screw may further include a groove and a driver interface. The driver interface of the screw may include a recess configured to receive or interface with a drive interface (e.g., a hexalobe drive, square drive, hex drive, torx drive, etc.) of the driver, thereby enabling the driver to drive the screw into the bone. The retaining sleeve may include one or more retention members configured to couple to the groove of the screw. In embodiments, the one or more retention members of the retaining sleeve may be configured to removably couple to the groove of the screw by a compression fit, a snap fit, or both. Utilizing a snap fit or compression fit to couple the retaining sleeve to the screw enables the screw to be coupled to the driver quickly, and may allow the screw to be automatically released or decoupled from the retaining member as the screw is driven flush with the bone.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions taken in conjunction with the accompanying drawings, in which:

FIG. 1 is a diagram illustrating a system for reducing a bone fracture in accordance with embodiments;

FIG. 2 is another diagram of a system for reducing a bone fracture in accordance with embodiments;

FIG. 13 is a diagram illustrating aspects of a reduction tool in accordance with embodiments;

FIG. 14 is a diagram illustrating additional aspects of a reduction tool in accordance with embodiments;

DETAILED DESCRIPTION

Referring to FIGS. 1-4, various diagrams illustrating aspects of a system for reducing a bone fracture in accordance with embodiments are shown as a system 100. In embodiments, the system 100 may be used to reduce a fracture of a bone. Additionally, the system 100 may enable compression to be maintained during insertion of a screw into the bone. In embodiments, the screw may be a headless screw.

Figure 3:
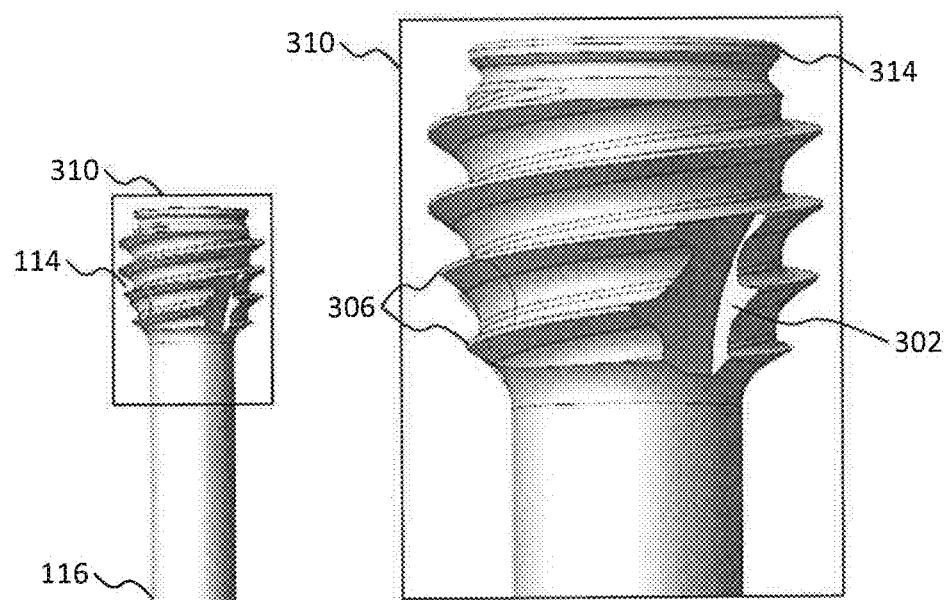
FIG. 3 is a diagram illustrating aspects of a screw for reducing a bone fracture in accordance with embodiments.
Figure 4:
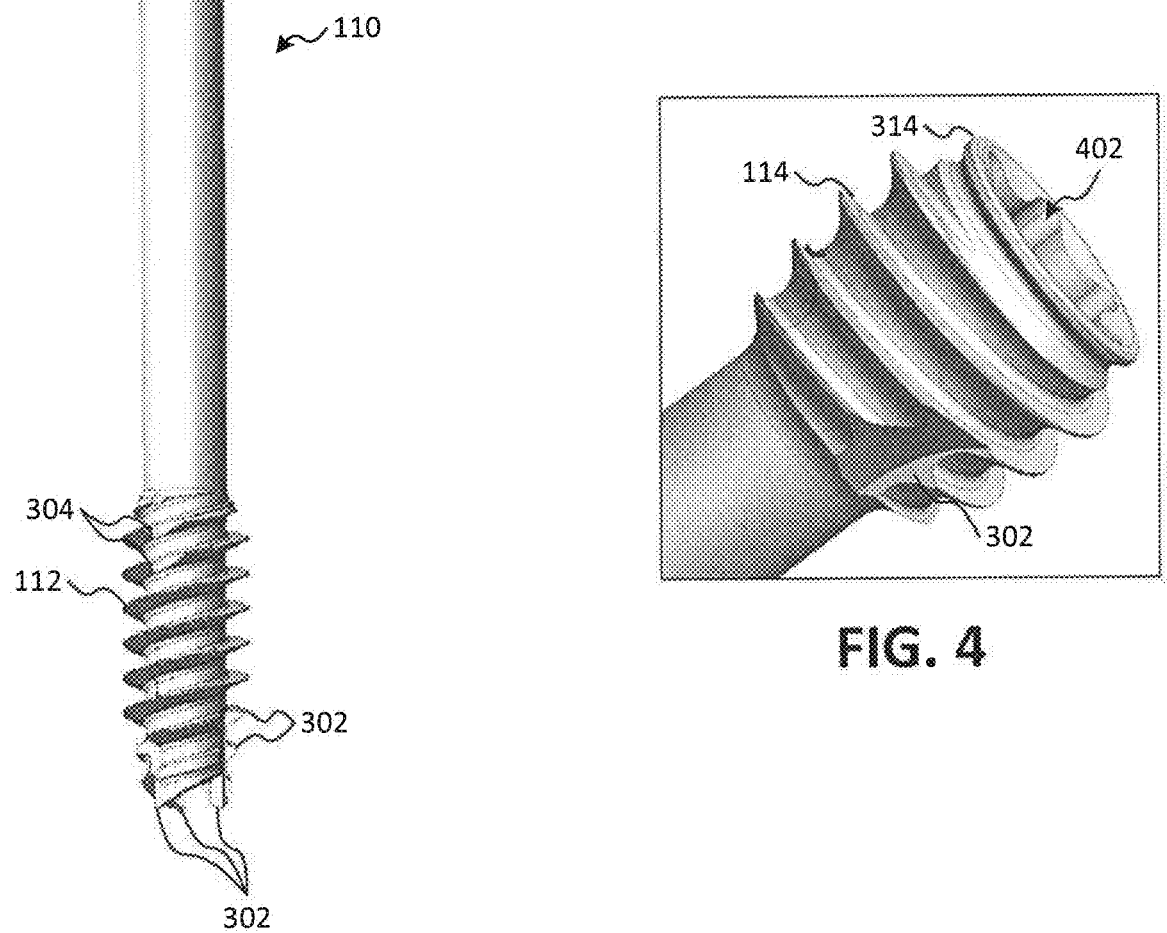
FIG. 4 is another diagram illustrating aspects of a screw for reducing a bone fracture in accordance with embodiments.

As shown in FIG. 1, the system 100 for providing reduction of a bone fracture may include a screw 110 and a reduction tool that includes a driver 130, a sleeve 120, a retaining sleeve 140, and a locking mechanism 150. The screw 110 may include a first threaded portion 112, a second threaded portion 114, and a non-threaded portion 116. In some embodiments, the screw 110 may be a cannulated screw. In other embodiments, the screw 110 may not be a cannulated screw. As shown in FIGS. 3 and 4, the first threaded portion 112 may correspond to a first end (e.g., a tip or lead portion) of the screw 110 and the second threaded portion 114 may correspond to a second end (e.g., a tail or trailing portion) of the screw 110. Each of the first threaded portion 112 and the second threaded portion 114 includes one or more threads. In embodiments, threads of the first threaded portion 112 and/or the threads of the second threaded portion 114 may be tapered, as shown in FIG. 3 at 306. This allows the threads to be more easily driven into a smaller size hole.

In embodiments, the first threaded portion 112 and the second threaded portion 114 may include one or more forward cutting flutes and/or reverse cutting flutes. For example, as shown in FIG. 3, the first threaded portion 112 includes three forward cutting flutes 302 and a plurality of reverse cutting flutes 304. It is noted that the particular number and location of cutting flutes and reverse cutting flutes illustrated with respect to FIGS. 3 and 4 are provided for purposes of illustration, rather than by way of limitation, and that embodiments contemplate screws with more forward cutting flutes and/or reverse cutting flutes than are illustrated in FIGS. 3 and 4 and/or screws with less cutting flutes and/or reverse cutting flutes than are illustrated in FIGS. 3 and 4. For example, in one embodiment, the first threaded portion 112 of the screw 110 may include two forward cutting flutes 302 and one reverse cutting flute 304, while in other embodiments, the first threaded portion 112 of the screw 110 may include one forward cutting flute 302 and two reverse cutting flutes 304. Thus, embodiments are not to be limited to a particular number and arrangement of forward cutting flutes and reverse cutting flutes.

In embodiments, the first threaded portion 112 and the second threaded portion 114 may include one or more threads and leads. In a particular embodiment, the first threaded portion 112 and the second threaded portion 114 may include two or more threads and two or more leads (e.g., the first threaded portion 112 and the second threaded portion 114 are at least double thread-double lead), which may enable the screw 110 to be driven into the bone faster. In still other embodiments, the first threaded portion 112 and the second threaded portion 114 may have the same number of threads and leads, or a different number of threads and leads. In some embodiments, the threads of the first threaded portion 112 and the threads of the second threaded portion 114 may have the same pitch. In other embodiments, the threads of the first threaded portion 112 and the threads of the second threaded portion 114 may have different pitches.

At callout 310 of FIG. 3, an enlarged diagram of the second threaded portion 114 of the screw 110 is shown. As shown in callout 310, the second end of the screw 110 may include a groove 314. As described in more detail below with respect to FIGS. 5A-5C, the groove 314 may be configured to enable the screw 110 to be coupled to the retaining sleeve 140. In some embodiments, the groove 314 may be formed as a ring that encircles the trailing end of the screw 110. In still other embodiments, the groove 314 may not be continuous (e.g., may not "encircle" the entire trailing end of the screw 110. In such embodiments, the trailing end of the screw 110 may have a groove formed by one or more groove portions disposed about the trailing end of the screw 110. The particular location and dimensions of the groove portions may be configured according to the configuration of the retaining sleeve 140 and its retention members, as described in more detail below. Additionally, as shown in FIG. 4, the second end of the screw 110 may include a driver interface 402. In an embodiment, the driver interface 402 may be formed as a recess configured to receive or interface with a drive interface (e.g., a hexalobe drive, square drive, hex drive, torx drive, etc.) of the driver 130, thereby enabling the driver 130 to drive the screw 110 into the bone.

The sleeve 120 may include a longitudinal bore extending along a length of the sleeve 120 between a first end of the sleeve 120 and a second end of the sleeve 120. The longitudinal bore of the sleeve 120 may be configured to enable the driver 130 to be inserted through the sleeve 120, as illustrated with respect to FIGS. 10 and 11. As described in more detail below with respect to FIG. 6, the longitudinal bore of the sleeve 120 may include a threaded portion. The driver 130 may include one or more threads configured to interface with the threaded portion of the longitudinal bore of the sleeve 120 when the driver 130 is inserted into the longitudinal bore of the sleeve 120, as described in more detail below.

The locking mechanism 150 may be configurable into a first state that locks the sleeve 120 to the driver 130 and a second state that unlocks the sleeve 120 from the driver 130. When the sleeve 120 is locked to the driver 130, rotation of the driver 130 may cause simultaneous rotation of the sleeve 120. When the sleeve 120 is unlocked from the driver 130, the driver 130 may be rotated independently from the sleeve 120 (e.g., the driver 130 may rotate freely within the sleeve 120).

The retaining sleeve 140 may be coupled to a first end of the driver 130. In an embodiment, the retaining sleeve 140 may be coupled to the first end of the driver 130. In embodiments, the retaining sleeve 140 may be coupled to the first end of the driver 130 via snap fit, a compression fit, a threaded fit, and the like, as described in more detail below. The retaining sleeve 140 may configured to couple to the screw 110. As described with more detail below with reference to FIGS. 5A-5C, when coupled to the screw 110, the retaining sleeve 140 may be configured to retain the screw 110 such that the drive interface of the driver 130 interfaces with the driver interface (e.g., driver interface 402 of FIG. 4) of the screw 110.

As shown in callout 160 of FIG. 2, when the retaining sleeve 140 is disposed within the sleeve 120 (e.g., when the locking mechanism 150 has locked the sleeve 120 to the driver 130), the interior surface of the longitudinal bore of the sleeve 120 may restrict movement of retention members (e.g., the retention members 142 of FIG. 5A) that couple the retaining sleeve 140 to the screw 110. Immobilization of the retention members of the retaining sleeve 140 may prevent the screw 110 from falling out of, or become dislodged from the reduction tool. This may simplify and improve handling of the reduction tool by a surgeon during reduction of a bone fracture.

In an embodiment, when the locking mechanism is configured into the first state, the retaining sleeve 140 and the proximal threads (e.g., the second threaded portion 114) of the screw 110 may be disposed entirely within the longitudinal bore of the sleeve. Retaining the proximal threads within the sleeve 120 may delay engagement of the proximal threads with the bone until compression is achieved with respect to a first fragment or section of the bone and a second fragment or section of the bone. In an additional or alternative embodiment, when the locking mechanism is configured into the first state, the retaining sleeve 140 and a first part of the proximal threads of the screw 110 may be disposed entirely within the longitudinal bore of the sleeve 120, and a second portion of the proximal threads of the screw may be disposed outside the sleeve, where the first part of the proximal threads of the screw 110 is larger than the second part of the proximal threads of the screw 110. This may allow a small portion of the proximal threads of the screw 110 to engage the bone to maintain compression while transitioning from the first state to the second state. However, it is noted that in embodiments where the proximal threads are entirely disposed within the sleeve 120 when in the first state, loss of compression may not occur (e.g., due to compressive forces applied to the bone by the sleeve 120, as described in more detail below with reference to FIG. 12) or may be trivial (e.g., can be recovered when the proximal threads are driven into the bone).

Figure 5A:
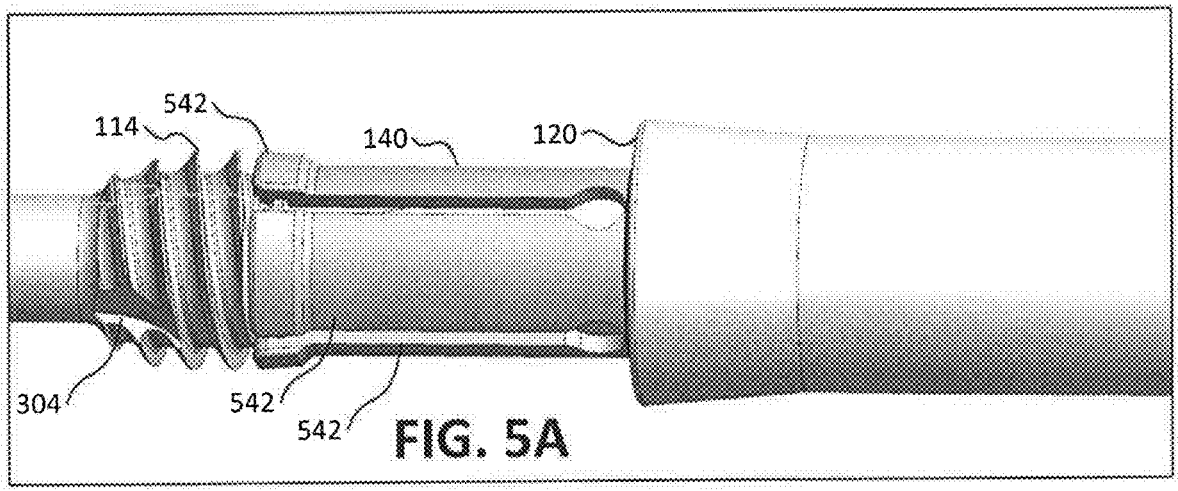
FIG. 5A is a diagram illustrating aspects of a retaining sleeve and screw in accordance with embodiments.
Figure 5B:
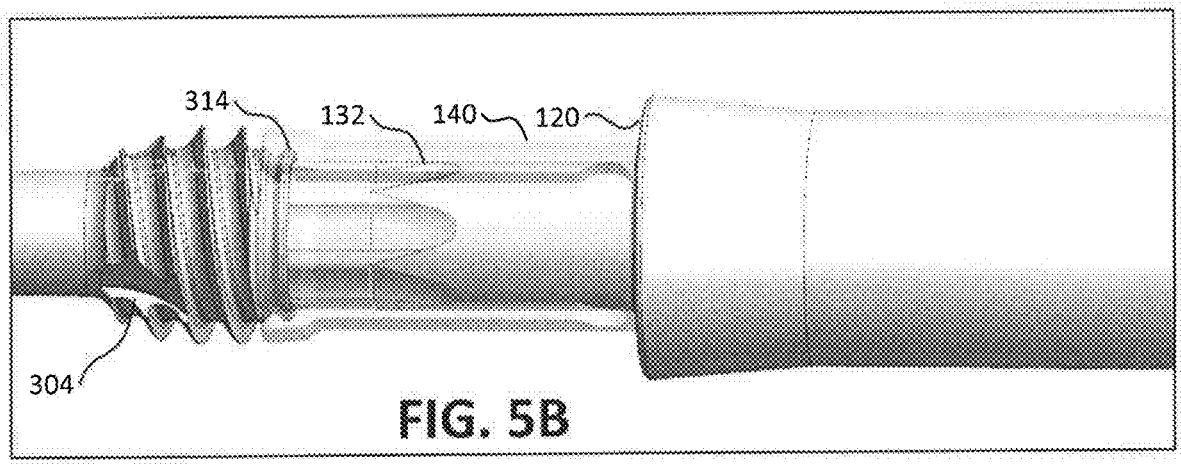
FIG. 5B is a diagram illustrating additional aspects of a retaining sleeve and screw in accordance with embodiments.
Figure 5C:
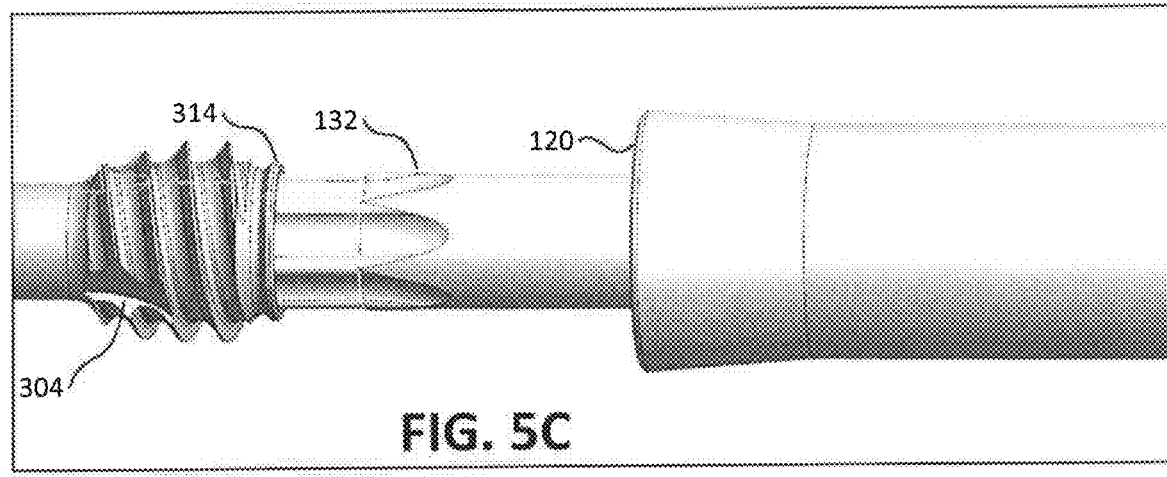
FIG. 5C is a diagram illustrating aspects of a driver and screw in accordance with embodiments.

Referring to FIGS. 5A-5C, diagrams illustrating aspects of a retaining sleeve, screw, and driver in accordance with embodiments are shown. As explained above with reference to FIGS. 3 and 4, a first end of the screw 110 may be a self-drilling tip having one or more first threads (e.g., the first threaded portion 112), and a second end of the screw 110 may include one or more second threads (e.g., second threaded portion 114) and a groove 314. As shown in FIG. 5A, the retaining sleeve 140 may include one or more retention members 542 configured to couple to the groove 314 of the screw 110. In an embodiment, at least a portion of the exterior edges of the retention members 542 may have a lip or ridge configured to slide over and rest behind the groove 314 of the screw 110, as shown in FIG. 5A. In embodiments, the retention members 542 may be resilient. This may provide a snap fit and/or a compression fit that allows the retaining sleeve 140 to hold the screw 110 using the groove 314, rather than the threads of the screw. As shown in FIG. 5B, the retaining sleeve 140 may surround the drive interface 132 of the driver 130 without preventing the drive interface 132 from being coupled to or inserted into the driver interface 402 of the screw 110.

Figure 6:
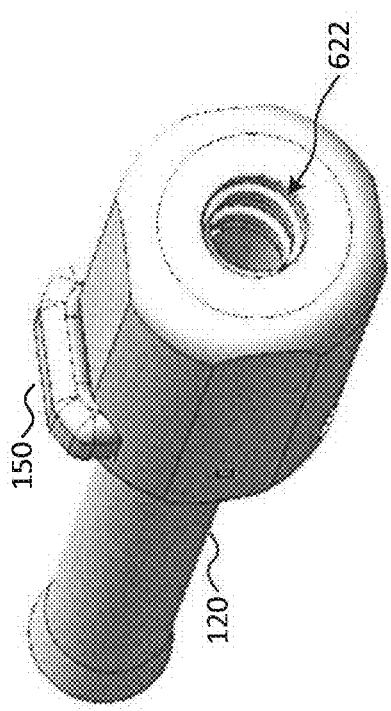
FIG. 6 is a diagram illustrating aspects of a sleeve for a reduction tool in accordance with embodiments.

Referring to FIG. 6, a diagram illustrating aspects of a sleeve for a reduction tool in accordance with embodiments is shown. As shown in FIG. 6, the sleeve 120 may include a longitudinal bore having a threaded portion 622. The threaded portion 622 of the longitudinal bore of the sleeve 120 may be configured to interface with one or more threads of the driver 130, as described in more detail below with reference to FIGS. 10 and 11. Additionally, as shown in FIG. 6, the sleeve 120 may be integrated with or may include the locking mechanism 150. In embodiments, the locking mechanism 150 may be a button disposed on or integrated with the sleeve 120, as described in more detail below.

Figure 7A:
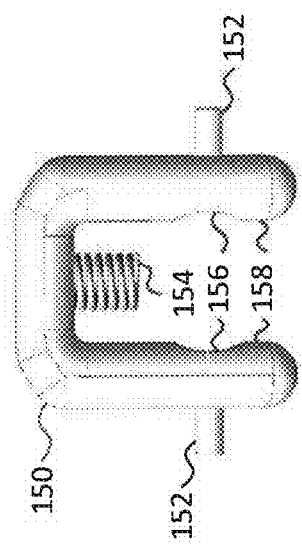
FIG. 7A is a diagram illustrating aspects of a locking mechanism for a reduction tool in accordance with embodiments.

Referring to FIG. 7A, a diagram illustrating aspects of a locking mechanism for a reduction tool in accordance with embodiments is shown. As shown in FIG. 7A, the locking mechanism 150 may include one or more pins 152 and a resilient member 154. The one or more pins 152 may be configured to couple the locking mechanism 150 with the sleeve 120, and the resilient member 154 may be configured to bias the locking mechanism 150 into a particular state. For example, in an embodiment, the resilient member 154 may bias the locking mechanism 150 into the first state (e.g., the locked state whereby the sleeve 120 is locked to the driver 130 such that rotation of the driver 130 rotates the sleeve 120 and rotation of the sleeve 120 rotates the driver 130). In embodiments, biasing the locking mechanism 150 into the first state does not necessarily mean that the locking mechanism 150 is actually in the first state. Instead, biasing the locking mechanism 150 into the first state indicates that the bias applied to the locking mechanism 150 by the resilient member 154 places the locking mechanism 150 into the first state and locks the sleeve 120 to the driver 130 when conditions are right (e.g., when the driver 130, the sleeve 120, and the locking mechanism 150 are in a proper locking orientation with respect to one another, as described with reference to FIG. 11). However, the locking mechanism 150 is maintained in the second state (e.g., the unlocked stated whereby the sleeve 120 is unlocked from the driver 130, allowing the sleeve 120 and the driver 130 to be rotated independent of each other) despite the bias applied to the locking mechanism 150 by the resilient member 154 when conditions are not right (e.g., the driver 130, the sleeve 120, and the locking mechanism are not in the proper locking orientation with respect to one another, as described with reference to FIG. 10). In embodiments, the resilient member 154 may be a spring. However, it is noted that illustration of the resilient member 154 as a spring is provided for purposes of illustration, rather than by way of limitation, and other types of resilient members may be used to bias the locking mechanism, such as.

As additionally shown in FIG. 7A, in embodiments, the locking mechanism 150 may include one or more curved interfaces 156 and one or more locking interfaces 158. In an embodiment, the curved interfaces 156 be disposed within the longitudinal bore of the sleeve 120 when the locking mechanism 150 is in the second state, and the one or more locking interfaces 158 of the locking mechanism 150 may be disposed within the longitudinal bore of the sleeve 120 when the locking mechanism 150 is in the first state. As described in more detail below with reference to FIG. 11, when the one or more locking interfaces 158 of the locking mechanism 150 are disposed within the longitudinal bore of the sleeve 120, the one or more locking interfaces 158 may engage one or more slots of the driver 130, restricting movement of the driver 130 along the longitudinal axis of the longitudinal bore of the sleeve 120 and locking the sleeve 120 to the driver 130. The one or more curved interfaces 156 may be configured with a curved surface that matches the interior surface of the longitudinal bore of the sleeve 120. Thus, when the one or more curved interfaces 156 of the locking mechanism 150 are disposed within the longitudinal bore of the sleeve 120, the one or more slots of the driver 130 are not engaged by the locking mechanism 150, which may unlock the sleeve 120 from the driver 130 to allow movement of the driver 130 along the longitudinal axis of the longitudinal bore of the sleeve 120.

Figure 7C:
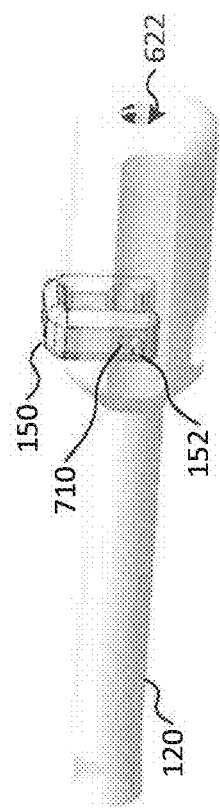
FIG. 7C is a diagram illustrating aspects of a locking mechanism, a sleeve, and a retaining sleeve for a reduction tool in accordance with embodiments.
Figure 7B:
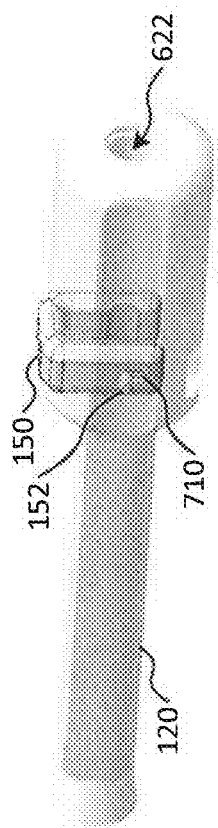
FIG. 7B is a diagram illustrating aspects of a locking mechanism and a sleeve for a reduction tool in accordance with embodiments.

Referring to FIGS. 7B and 7C, diagrams illustrating aspects of a locking mechanism and a sleeve for a reduction tool in accordance with embodiments are shown. As shown in FIGS. 7B and 7C, the locking mechanism 150 may comprise one or more channels 710. The pins 152 may be slidably disposed within the one or more channels 710. For example, in FIG. 7B, the pins 152 are slidably disposed within an upper portion of the one or more channels 710, and in FIG. 7B, the pins 152 are slidably disposed within a lower portion of the one or more channels 710. The pins 152 may be fixedly coupled to the interior of the sleeve 120. In such an arrangement, the locking mechanism 150 may be operated as a button. For example, in FIG. 7B, the locking mechanism 150 may be pressed down to place the locking mechanism 150 in the second state (e.g., to unlock the sleeve 120 from the driver 130). When the locking mechanism 150 is released, the resilient member 154 may apply the bias force to the locking mechanism 150. This may not necessarily place the locking mechanism 150 into the first state (e.g., the locked state). For example, upon release, the locking mechanism 150 may remain in the unlocked state until conditions are right (e.g., until the driver 130, the sleeve 120, and the locking mechanism 150 are in a proper locking orientation with respect to one another, as described with reference to FIG. 11). Additionally, it is noted that, when in the first state, the retaining sleeve 140 (not shown in FIG. 7C) may be disposed within the sleeve 120, as described in more detail below with respect to FIG. 11.

Figure 8:
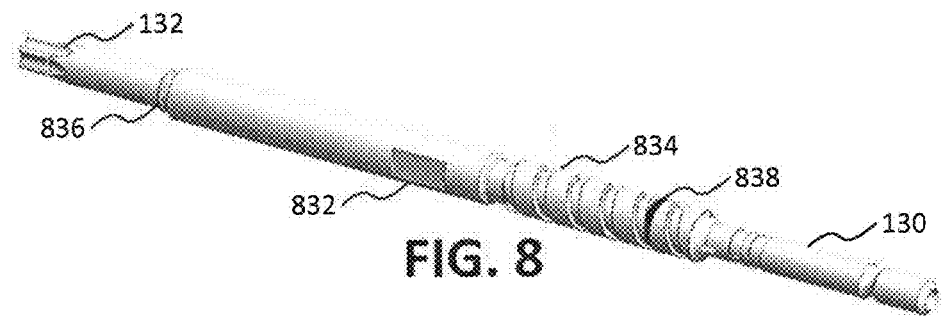
FIG. 8 is a diagram illustrating aspects of a driver for a reduction tool in accordance with embodiments.
Figure 9:
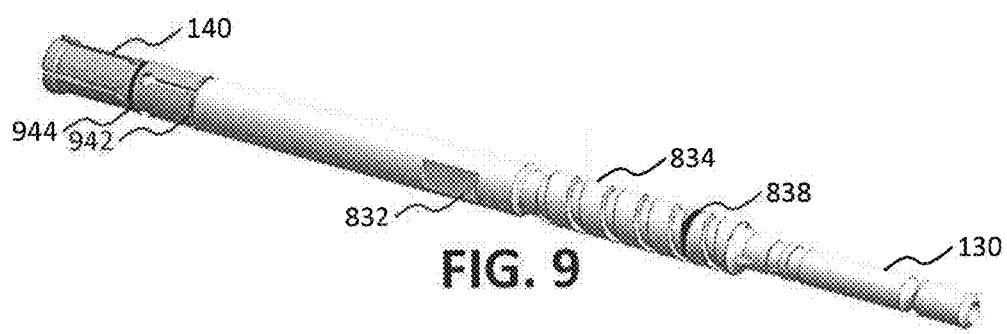
FIG. 9 is a diagram illustrating aspects of a driver coupled to a retaining sleeve in accordance with embodiments.

FIG. 8 is a diagram illustrating aspects of a driver for a reduction tool in accordance with embodiments. As shown in FIG. 8, a drive interface 132 may be located at a first end of the driver 130. As described above with reference to FIG. 4, the drive interface 132 is configured to mate with the driver interface of the screw (e.g., the driver interface 402 of FIG. 4), enabling the driver 130 to drive be rotated to drive the screw into the bone (or remove the screw from the bone). As shown in FIG. 8, the driver 130 includes one or more notches 832. As described in more detail below, and as illustrated with reference to FIGS. 10 and 11, when the locking mechanism 150 is configured into the first state, the locking mechanism 150 may engage the one or more notches 832 of the driver 130, thereby locking the sleeve 120 (not shown in FIG. 8) to the driver 130. The driver 130 further includes one or more threads 834. The threads 834 may be configured to interface with a threaded portion of the longitudinal bore of the sleeve 120 (e.g., the threaded portion 622 of FIG. 6). In embodiments, the one or more threads 834 may be configured to align the one or more notches 832 with the locking mechanism 150, as described in more detail below with reference to FIGS. 10 and 11. The driver 130 may include a retaining sleeve interface 836. The retaining sleeve interface 836 may be configured to couple the retaining sleeve 140 to the driver 130, as shown in FIG. 9. In embodiments, the retaining sleeve interface 836 may comprise a groove configured to removably couple the retaining sleeve 140 to the driver 130 via a compression fit, a snap fit, and the like. In additional or alternative embodiments, the retaining sleeve 140 may be coupled to the driver 130 via another coupling technique, such as via a threaded fit. However, it is noted that the retaining sleeve is not coupled to the screw via a threaded fit.

In embodiments, one or more visual indicators may be provided. Each of the one or more visual indicators may correspond to one or more operational states of the reduction tool. For example, as illustrated in FIG. 8, the driver 130 may include a visual indicator 838, which may correspond to an operational state that indicates the screw 110 has been driven into and is flush with a surface of the bone. As shown in FIG. 9, in embodiments, the retaining sleeve 140 may include a visual indicator 944, which may correspond to an operational state that indicates the retaining sleeve 140 may be removably coupled to the screw. For example, the one or more threads 834 may be used to expose the retaining sleeve 140 outside the sleeve 120, such as to couple the retaining sleeve 140 to a screw. Rotation of the driver 130 in a first direction may advance the retaining sleeve 140 out of the sleeve 120, and rotation of the driver 130 in a second direction may draw the retaining sleeve 140 into the sleeve 120. When the driver 130 is rotated in the first direction, the visual indicator 944, when visible, may signify that the retaining sleeve 140 has been advanced out of the sleeve 120 by an amount sufficient to enable the retaining sleeve 140 to removably couple to a screw (e.g., the interior surface of the longitudinal bore of the sleeve 120 no longer restricts movement of the retention members 142).

Figure 10:
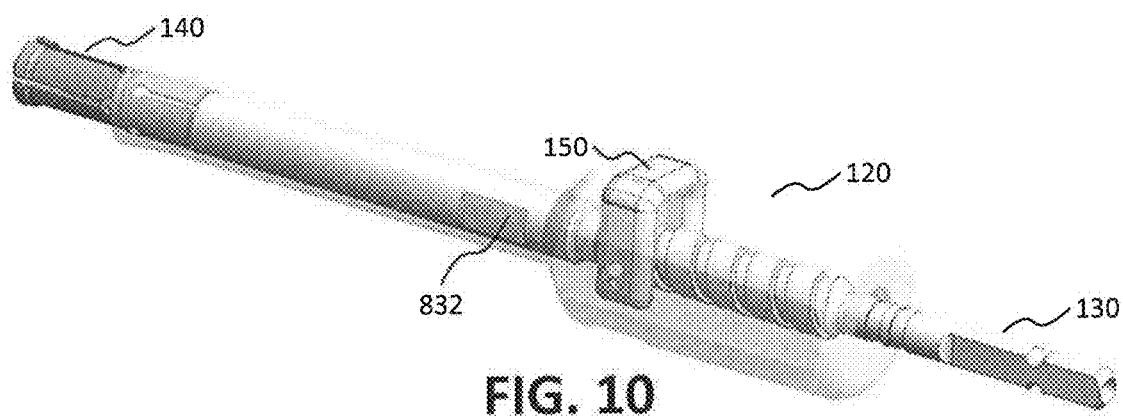
FIG. 10 is a diagram illustrating aspects of a driver and reduction tool inserted into a sleeve in an unlocked state in accordance with embodiments.
Figure 11:
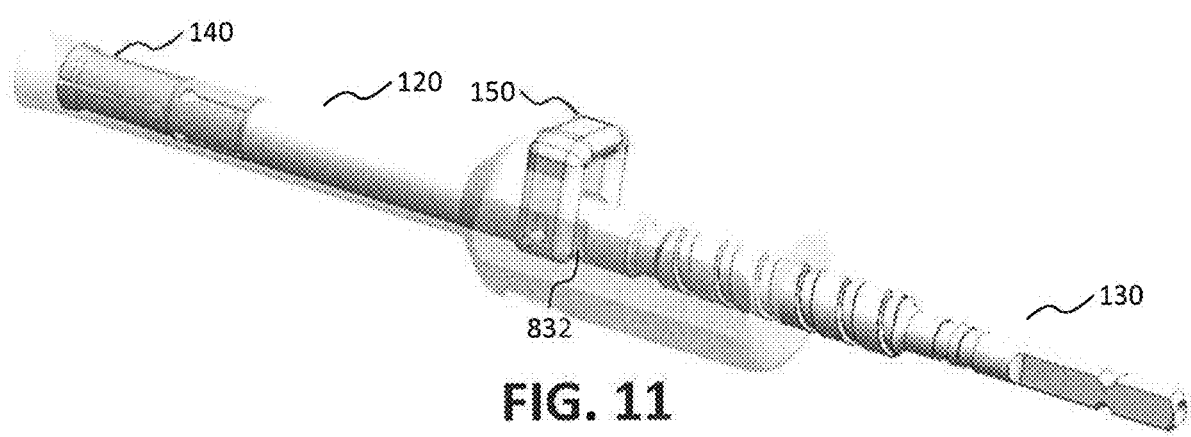
FIG. 11 is a diagram illustrating aspects of a driver and reduction tool inserted into a sleeve in a locked state in accordance with embodiments.

Referring to FIG. 10, a diagram illustrating aspects of a driver and reduction tool inserted into a sleeve in an unlocked state in accordance with embodiments is shown. As shown in FIG. 10, the locking mechanism 150 is in the second stated (e.g., the unlocked state) because the locking interfaces (not labeled in FIG. 10) of the locking mechanism 150 are not engaging the one or more slots 832 of the driver 130. As the driver 130 is rotated in a particular direction (e.g., counterclockwise), the interfacing of the threads of the driver 130 with the threaded portion of the longitudinal bore of the sleeve 120 may retract the driver 130, pulling the retaining sleeve 140 into the sleeve 120. As the driver 130 is retracted, the one or more slots 832 of the driver 130 may move towards the locking mechanism 150. In embodiments, the threads of the driver 130 and the threaded portion of the longitudinal bore of the sleeve 120 may be configured to bring the one or more slots into alignment with the locking mechanism 150. Once in alignment, the one or more locking interfaces of the locking mechanism 150 may engage the one or more slots 832 (e.g., due to the bias applied to the locking mechanism 150 by the resilient member 154 of FIG. 7A-7C), as shown in FIG. 11. This may configure the locking mechanism 150 into the first state and may lock the sleeve 120 to the driver 130 such that rotation of the driver 130 causes rotation of the sleeve 120 and vice versa. As shown in FIG. 11, while in the first state, the retaining sleeve 140 may be disposed entirely within the sleeve 120.

Figure 12:
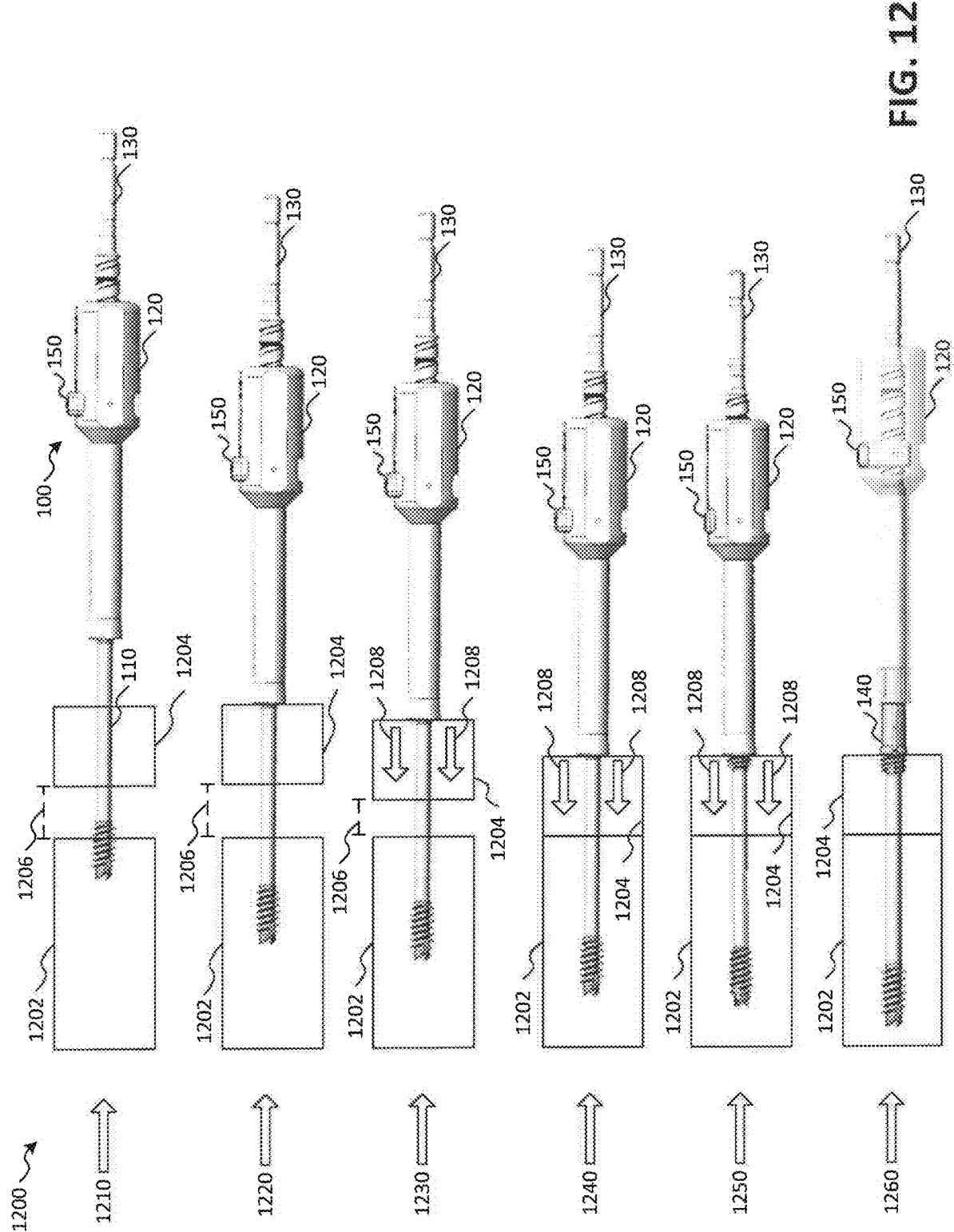
FIG. 12 is a diagram illustrating aspects of a method for reducing a bone fracture using a reduction tool in accordance with embodiments.

Referring to FIG. 12, a diagram illustrating aspects of a method for reducing a bone fracture using a reduction tool in accordance with embodiments is shown. As shown in FIG. 12, at 1210, the locking mechanism 150 may be placed in the first state, the retaining sleeve may be disposed within the sleeve 120, and the screw 110 may be driven into a bone fracture. It is noted that in FIG. 12, the bone fracture comprises a first bone fragment or section 1202 and a second bone fragment or section 1204, where the first bone fragment or section 1202 and the second bone fragment or section 1204 are separated by a distance 1206. In order to improve the healing of the bone fracture, distance 1206 between the first bone fragment or section 1202 and the second bone fragment or section 1204 should be reduced to facilitate compression between the first bone fragment or section 1202 and the second bone fragment or section 1204.

At 1220, the distal threads (e.g., the first threaded portion 112) of the screw 110 have been driven further into the bone fragments and the proximal end of the sleeve 120 is now adjacent to the second bone fragment or section 1204. Additionally, the non-threaded portion (e.g., the non-threaded portion 116) of the screw 110 passes through the second bone fragment or section 1204. However, at 1220, the distance 1206 separating the first bone fragment or section 1202 and the second bone fragment or section 1204 has not been reduced. At 1230, the distal threads of the screw 110 have been driven further into the bone fragments and the proximal end of the sleeve 120 remains adjacent to the second bone fragment or section 1204. As the distal threads were driven further into the bone fragments or sections, the proximal end of the sleeve 120 applies a compressive force 1208 to the second bone fragment or section 1204, which has reduced the distance 1206 separating the first bone fragment or section 1202 and the second bone fragment or section 1204. However, there may not be a suitable amount of compression present yet. At 1240, the distal threads of the screw 110 have been driven further into the bone fragments while maintaining the proximal end of the sleeve 120 adjacent to the second bone fragment or section 1204. As the distal threads were driven further into the bone fragments or sections, the proximal end of the sleeve 120 continued to apply the compressive force 1208 to the second bone fragment or section 1204, which has reduced the distance 1206 separating the first bone fragment or section 1202 and the second bone fragment or section 1204, and a suitable amount of compression is now present between the first bone fragment or section 1202 and the second bone fragment or section 1204.

At 1250, the locking mechanism 150 is depressed, causing the locking interfaces of the locking mechanism to disengage the one or more slots of the driver 130. This allows the driver 130 be rotated independent of the sleeve 120, enabling proximal threads (e.g., the second threaded portion 114) of the screw 110 to engage the second bone fragment or section 1204. In embodiments, when the surgeon depresses the locking mechanism 150 to unlock the sleeve 120 from the driver 130, the surgeon may hold the sleeve 120 to maintain the compressive force 1208 until the proximal threads of the screw engage the second bone fragment or section 1204. This prevents loss of compression between the first bone fragment or section 1202 and the second bone fragment or section 1204. In other embodiments, the compression may be maintained due to the engagement of the threads of the driver 130 with the threaded portion of the longitudinal bore of the sleeve 120. At 1260, the visual indicator of the retaining sleeve 140 is now visible, signifying that the screw 110 has been driven completely into and flush with the exterior surface of the second bone fragment or section 1204. It is noted that, in some embodiments, the visual indicator may become visible due to the interaction of the threads of the driver 130 and the threaded portion of the longitudinal bore of the sleeve 120. For example, as the driver 130 is rotated, the threads of the driver 130 may advance the driver 130 through the longitudinal bore of the sleeve 120, causing the retaining sleeve 140 to exit the proximal end of the sleeve 120 and allowing the visual indicator to be seen. As shown at 1260, the retaining sleeve 140 has exited the sleeve 120, allowing the retaining sleeve 140 to be released from the screw 110. In some embodiments, the screw 110 may be released from the retaining sleeve 140 automatically as the screw 110 is driven flush with the bone. For example, as the screw 110 drives into the bone and the retaining sleeve 140 comes into contact with the bone, the bone may press against the retaining sleeve 140 and this force may cause the retention members of the retaining sleeve 140 to release or disengage the screw 110.

As shown above, the method 1200 and the system 100 of embodiments provides a screw and reduction tool configured to provide improved compression when reducing a fracture using a headless screw. Further, the reduction tool of embodiments does not require components, such as a driver, to be removed or exchanged during driving of the screw into the bone. This simplifies the process and reduces the likelihood that compression is lost. Thus, the screw 110 and the reduction tool (e.g., the sleeve 120, the driver 130, the retaining sleeve 140 and the locking mechanism 150) of the system 100 provide improved techniques for providing compression when reducing a bone fracture. It is noted that the reduction tool of embodiments may be further coupled to a drill or other external tool (not shown) configured to couple to and cause rotation of the driver 130.

Figure 15:
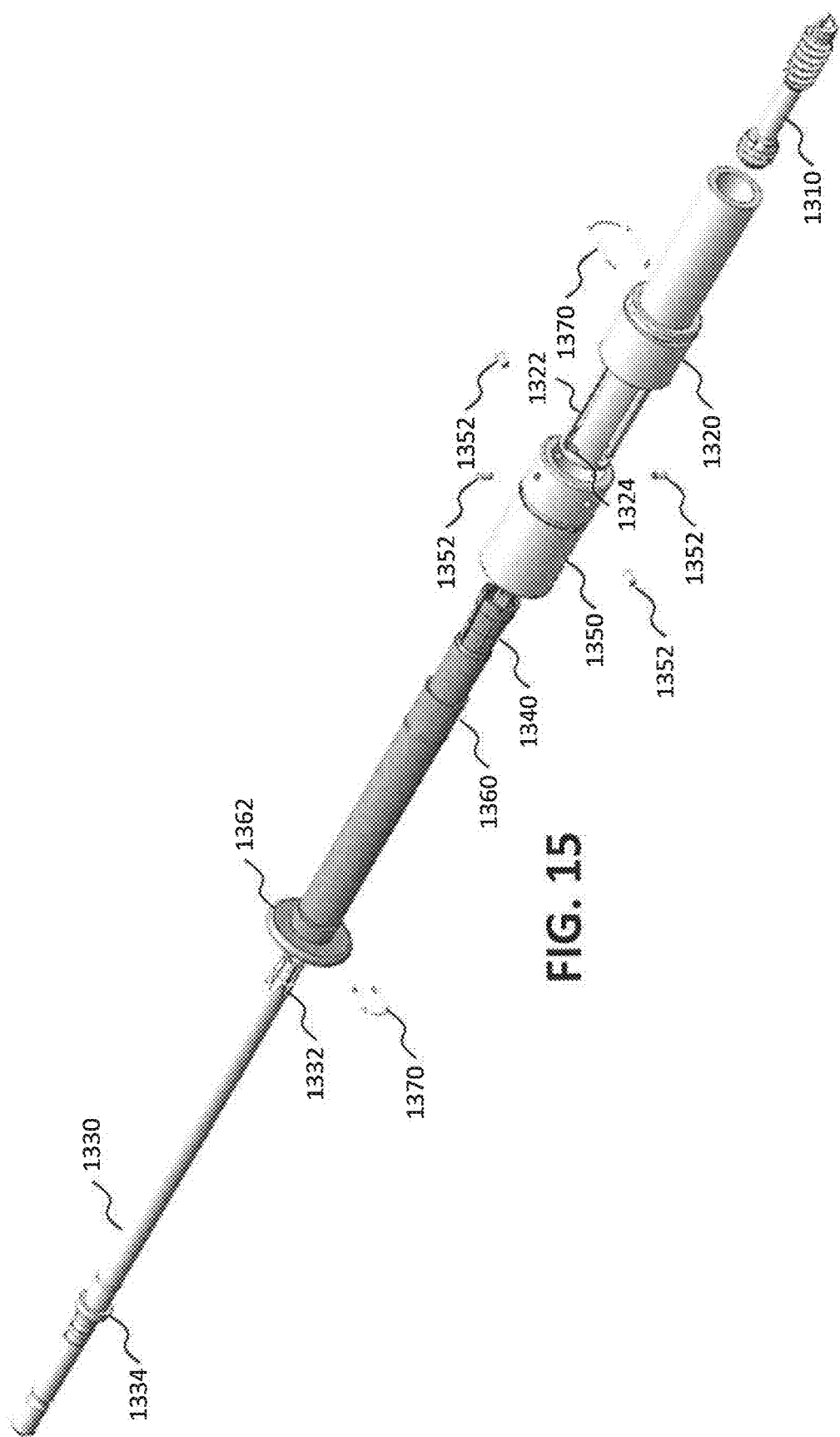
FIG. 15 is a exploded diagram illustrating additional aspects of a reduction tool in accordance with embodiments.

Referring to FIGS. 13-15, diagrams illustrating another embodiment of a system for providing improved compression during reduction of a bone fracture are shown as a system 1300. It is noted that the system 1300 incorporates various aspects of the system 100 described above, such as providing a reduction tool including a retaining sleeve that releasably couples to a headless screw having a groove (e.g., the groove 314 of FIGS. 3 and 4), and that enables compression to be maintained during driving of a screw into a bone without requiring removal or exchanging of components of the reduction tool. However, the system 1300 achieves some of these aspects utilizing different techniques, as will be apparent from the description that follows.

In embodiments, the system 1300 includes a screw 1310 and a reduction tool that includes an outer sleeve 1320, a driver 1330, a retaining sleeve 1340, a locking sleeve 1350, and an inner sleeve 1360. In embodiments, the screw 1310 may be the screw 110 of FIGS. 1-12. For example, the screw 1310 may include a first threaded portion (e.g., distal threads), a non-threaded portion, and a second threaded portion (e.g., proximal threads). The first threaded portion of the screw 1310 may be configured as described above with respect to the first threaded portion 112 of the screw 110 and the second threaded portion of the screw 1310 may be configured as described above with respect to the second threaded portion 114 of the screw 110. For example, the first and second threaded portions of the screw 1310 may each include one or more cutting flutes, reverse cutting flutes, one or more threads (e.g., single thread-single lead threads, double thread-double lead threads, etc.), tapered threads, threads having different pitches, and the like. In some embodiments, the screw 1310 may be a cannulated screw. In other embodiments, the screw 1310 may be a non-cannulated screw. Additionally, the screw 1310 may include a groove (e.g., the groove 314 of FIGS. 3 and 4) configured to enable the screw 1310 to be coupled to the retaining sleeve 1340. In embodiments, the screw 1310 may be coupled to the retaining sleeve 1340 as described above with respect to the screw 110 and the retaining sleeve 140 with reference to FIGS. 5A-5C. Additionally, the screw 1310 may include a driver interface (e.g., the driver interface 402 of FIG. 4) configured to interface with a drive interface 1332 of the driver 1330. The drive interface 1332 may be the drive interface 132 described above with respect to the driver 130, and may enable the driver 1330 to drive the screw 1310 into a bone.

The inner sleeve 1360 may include a longitudinal bore extending along a length of the inner sleeve 1360 between a first end of the inner sleeve 1360 and a second end of the inner sleeve 1360. The longitudinal bore of the inner sleeve 1360 may be configured to enable the driver 1330 to be inserted through the inner sleeve 1360. Additionally, the inner sleeve includes the retaining sleeve 1340 configured to couple to the screw 1310, as described above with respect to coupling the retaining sleeve 140 to the screw 110 with reference to FIGS. 5A-5C, and includes a driver interface 1362. The driver interface 1362 may be configured to provide a compressive force as the screw 1310 is driven into the bone, as described in detail with reference to FIG. 16. In embodiments, the driver interface 1362 may be configured to interface with an inner sleeve interface 1334 of the driver 1330. During driving of the screw 1310 into the bone, the inner sleeve interface 1334 of the driver 1330 may apply a compressive force to the driver interface 1362 of the inner sleeve 1360.

In embodiments, the driver interface 1362 may be a plate disposed on a first end of the inner sleeve 1360, as shown in FIG. 15, where the retaining sleeve 1340 is coupled to integrated with the inner sleeve 1360 at a second end of the inner sleeve 1360. In other embodiments, the driver interface 1362 may be provided by a thickened portion of the exterior wall of the inner sleeve 1360. In embodiments, the inner sleeve interface 1334 of the driver 1330 may comprise a ridge that extends outward around the exterior surface of the driver 1330 such that when the driver 1330 is inserted through the longitudinal bore of the inner sleeve 1360, the ridge comes into contact with the driver interface 1362. In additional or alternative embodiments, the driver interface 1362 may be formed as a recess at the first end of the inner sleeve 1360 and the inner sleeve interface 1334 may formed as a shape configured to be received by the recess of the inner sleeve (e.g., similar to mating of the drive interface 1332 of the driver 1330 with the driver interface of the screw 1310). It is noted that the particular implementations or configurations of the inner sleeve interface 1334 of the driver 1330 and the driver interface 1362 of the inner sleeve 1360 described herein are provided for purposes of illustration, rather than by way of limitation, and that embodiments should not be limited to the specific exemplary configurations described herein. For example, the inner sleeve interface 1334 of the driver 1330 and the driver interface 1362 of the inner sleeve 1360 may have any configuration that enables the inner sleeve 1360 to apply a compressive force to the driver interface 1362 during driving of a screw into the bone.

The locking sleeve 1350 may include a longitudinal bore configured to enable insertion of the outer sleeve 1320 through the locking sleeve 1350. The longitudinal bore of the locking sleeve 1350 may extend along a length of the locking sleeve 1350 between a first end of the locking sleeve 1350 and a second end of the locking sleeve 1350. In embodiments, the locking sleeve 1350 is configurable into a first state that locks the locking sleeve 1350 to the outer sleeve 1320 and a second state that unlocks the outer sleeve 1320 from locking sleeve 1350. In the first state, the retaining sleeve 1340 may be prevented from exiting the outer sleeve 1320, and in the second state, the retaining sleeve 1340 may be enabled to exit the outer sleeve 1320. Additionally, when the locking sleeve 1350 is configured into the first state, the compressive force applied (e.g., by the inner sleeve interface 1334 of the driver 1330) to the driver interface 1362 of the inner sleeve 1360 may be transferred to the bone via the locking sleeve 1350 and the outer sleeve 1320. When the locking sleeve 1350 is configured into the second state, the compressive force applied (e.g., by the inner sleeve interface 1334 of the driver 1330) to the driver interface 1362 of the inner sleeve 1360 is transferred to the bone via the inner sleeve 1360 and the retaining sleeve 1340.

The outer sleeve 1320 may include a longitudinal bore configured to enable insertion of the inner sleeve through the outer sleeve. The longitudinal bore of the inner sleeve 1360 may extend along a length of the outer sleeve 1320 between a first end of the outer sleeve 1320 and a second end of the outer sleeve 1320. In embodiments, the outer sleeve 1320 may include one or more channels, each of the one or more channels comprising a first channel portion 1322 and a second channel portion 1324. In some embodiments, the second channel portion 1324 may be perpendicular to the first channel portion 1322. In other embodiments, the second channel portion 1324 may form an acute angle with respect to the first channel portion 1322. The locking sleeve 1350 may include one or more pins 1352 disposed within the longitudinal bore of the locking sleeve 1350. Each of the one or more pins 1352 may be configured to slidably engage a corresponding one of the one or more channels of the outer sleeve 1320. The locking sleeve 1350 may be configured into the second state when the one or more pins 1352 are slidably engaged with the first channel portion 1322 of the corresponding ones of the one or more channels of the outer sleeve 1320, and the locking sleeve 1350 may be configured into the first state when the one or more pins are slidably engaged with the second channel portion 1324 of the corresponding ones of the one or more channels of the outer sleeve 1320. For example, to transition the locking sleeve 1350 from the first state to the second state, the locking sleeve 1350 may be slid down the channel until the second channel portion 1324 diverges from the first channel portion 1322, and then rotating the locking sleeve 1350 in a first direction to direct the pins 1352 into the second channel portion 1324. To transition the locking sleeve 1350 from the second state to the first state, the locking sleeve 1350 may be rotated in a second direction until the pins 1352 are aligned with the first channel portion 1322. In some embodiments, one or more clips 1370 may be provided. The one or more clips 1370 may be resilient and configured to apply pressure to the one or more components of the tool to prevent the different components from sliding apart easily, which may simplify handling of the tool. For example, outer sleeve 1320 may be provided with a clip 1370 configured to apply pressure to (e.g., a pinch or squeeze) the inner sleeve 1360 which may prevent the inner sleeve 1360 from easily sliding out of the outer sleeve 1320. In other embodiments, the different sleeves of the tool may be prevented from easily sliding using a friction fit, or another technique.

Figure 16:
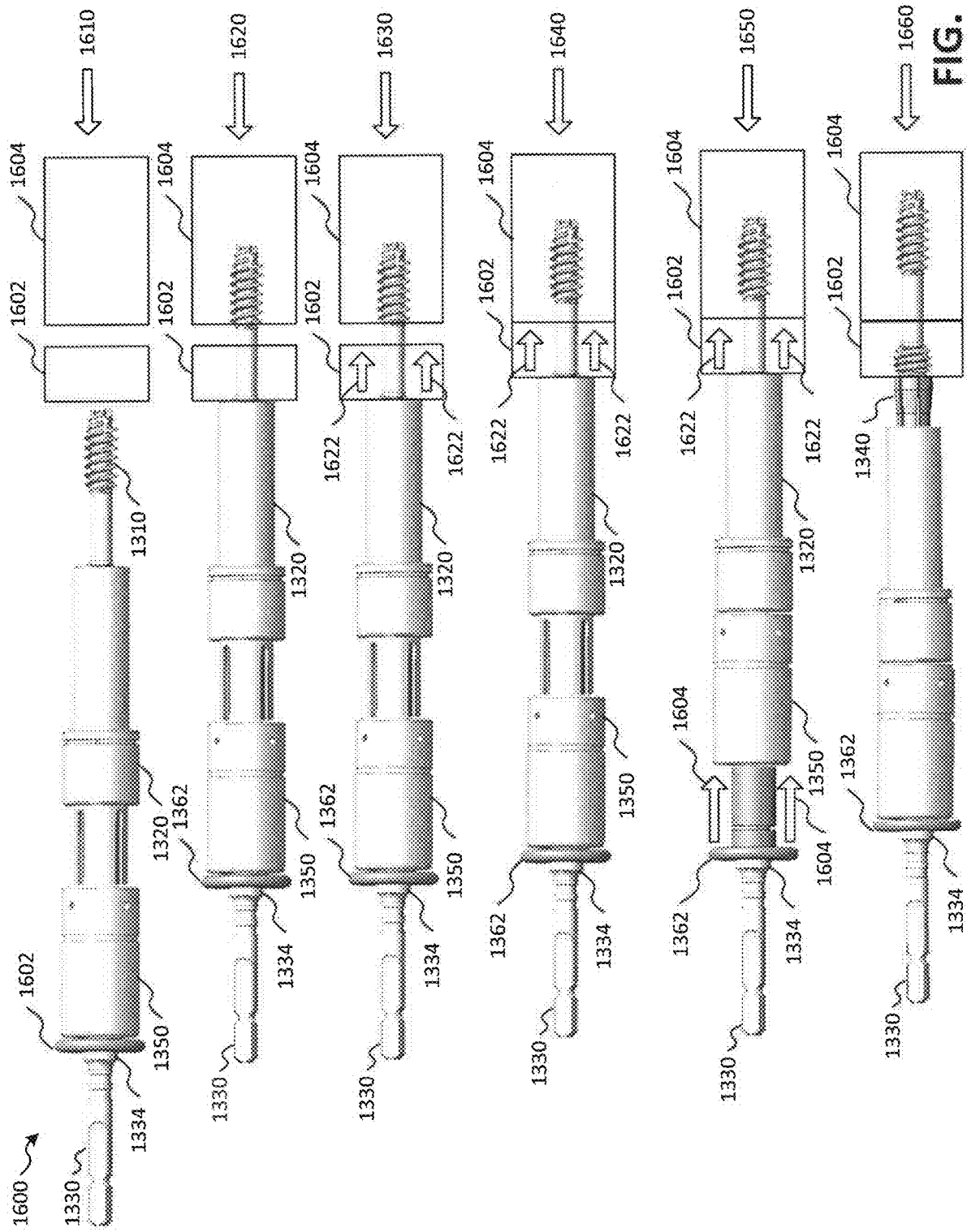
FIG. 16 is a diagram illustrating aspects of a method for reducing a bone fracture using a reduction tool in accordance with embodiments.

Referring to FIG. 16, a diagram illustrating aspects of a method for reducing a bone fracture using a reduction tool in accordance with embodiments. As shown in FIG. 16, at 1610, the screw 1310 has been coupled to the retaining sleeve 1340 and the locking sleeve has been configured into the first state (e.g., the locked state). It is noted that the locking sleeve 1350 may have been configured into the second state (e.g., the unlocked state) when the screw 1310 was coupled to the retaining sleeve 1340. This is because the second state enables the retaining sleeve 1340 to exit the outer sleeve 1320, allowing retaining members (not shown in FIG. 16) of the retaining sleeve 1340 to couple to the groove of the screw 1310. As described above with reference to FIGS. 1-12, while retained within the outer sleeve 1320, the screw 1310 may be lockably held by the retaining sleeve 1340 (e.g., because the retaining members cannot move in a manner sufficient to enable the ridges at the ends of the retaining members to release from the groove of the screw 1310). Once the screw has been coupled to the retaining sleeve 1340 and the locking sleeve 1350 has been configured into the first state, the tool may be ready for use in reducing a fracture. For example, in FIG. 16, a fracture of a bone is shown and includes a first bone fragment or section 1602 and a second bone fragment or section 1604 separated by a distance (not labeled in FIG. 16).

At 1620, the screw 1310 has been driven into the first bone fragment or section 1602 and the second bone fragment or section 1604, and the proximal end of the outer sleeve 1320 is adjacent the first bone fragment or section 1602. As explained above with reference to FIG. 12, by bringing the proximal end of the outer sleeve 1320 adjacent to the bone fragment or section, a compressive force may be applied to the bone fragment or section to reduce the distance separating the first bone fragment or section 1602 and the second bone fragment or section 1604. Accordingly, at 1630, as the screw 1310 is driven further into the first bone fragment or section 1602 and the second bone fragment or section 1604, a compressive force 1622 is applied. In FIG. 16, the inner sleeve interface 1334 of the driver 1330 initially applies the compressive force 1622 to the driver interface 1362 of the inner sleeve. As shown in FIG. 16, when in the first state (e.g., the locked state), the locking sleeve 1350 is locked to the outer sleeve 1320 and thus cannot move towards the proximal end of the outer sleeve 1320. Additionally, as shown in FIG. 16, when in the first state, the locking sleeve 1350 is adjacent to the driver interface 1362 of the inner sleeve 1360. As the driver drives the screw 1310 into the bone, the inner sleeve interface 1334 of the driver 1330 applies the compressive force 1622 to of driver interface 1362 of the inner sleeve 1360. Because the locking sleeve 1350 is adjacent to the driver interface 1362 of the inner sleeve 1360, and because the locking sleeve 1350 is locked to the outer sleeve 1320 having its proximal end adjacent to the first bone fragment or section 1602, the compressive force is then transferred to or applied to the first bone fragment or section 1602 via the locking sleeve 1350 and the outer sleeve 1320.

As shown at 1640, the compressive force 1622 may reduce the distance that separates the first bone fragment or section 1602 and the second bone fragment or section 1604 until a desired amount of compression is achieved. Once the bone fracture has been sufficiently reduced and the desired amount of compression has been achieved, the locking sleeve 1350 may be configured into the second state (e.g., the unlocked state) by rotating the locking sleeve 1350 in the second direction until the pins 1352 are aligned with the first channel portions 1322. Once aligned with the first channel portions 1322, the compressive force 1622 may urge the pins 1352 into the first channel portions 1322, transitioning the locking sleeve from the first state to the second state, as shown at 1650. As explained above, when the locking sleeve 1350 is configured into the second state, the compressive force 1622 applied (e.g., by the inner sleeve interface 1334 of the driver 1330) to the driver interface 1362 of the inner sleeve 1360 is transferred to the bone via the inner sleeve 1360 and the retaining sleeve 1340, as shown at 1660. In some embodiments, the retaining sleeve 1340 may not exit the outer sleeve 1320 despite the screw 1310 having been driven completely into and flush with the surface of the bone. For example, because the outer sleeve 1320 enables the inner sleeve 1360 to pass through the longitudinal bore of the outer sleeve 1320, and because there are no threads in the outer sleeve 1320's longitudinal bore, the outer sleeve 1320 may remain adjacent to the bone until the driving of screw 1310 is complete. However, in some embodiments, the outer sleeve 1320 may be slid towards the driver interface 1362 as the driving of the screw comes closer to completion, as this may enable the surgeon to view a visible indicator of the retaining sleeve 1340 that indicates when the screw 1310 has been completely driven into and flush with the bone. In still other embodiments, the visual indicator may be provided on the inner sleeve 1360, rather than the retaining sleeve 1340, such as a visual indicator that indicates the driving of the screw 1310 is completed when then visual indicator reaches the end of the locking sleeve 1350 nearest the driver interface 1362. As shown at 1660, the retaining sleeve 1340 has exited the outer sleeve 1320, allowing the retaining sleeve 1340 to be released from the screw 1310. In some embodiments, the screw 1310 may be released from the retaining sleeve 1340 automatically as the screw 1310 is driven flush with the bone. For example, as the screw 1310 drives into the bone and the retaining sleeve 1340 comes into contact with the bone, the bone may press against the retaining sleeve 1340 and this force may cause the retention members of the retaining sleeve 1340 to release or disengage the screw 1310.

As shown above, the method 1600 and the system of embodiments illustrated with respect to FIGS. 13-16 provide a screw and reduction tool configured to provide improved compression when reducing a fracture using a headless screw. Further, the reduction tool of embodiments does not require components, such as a driver, to be removed or exchanged during driving of the screw into the bone. This simplifies the process and reduces the likelihood that compression is lost. Thus, the screw 1310 and the reduction tool (e.g., the outer sleeve 1320, the driver 1330, the retaining sleeve 1340, the locking sleeve 1350, and the inner sleeve 1360) of the system illustrated with respect to FIGS. 13-16 provide improved techniques for providing compression when reducing a bone fracture. It is noted that the reduction tool of embodiments may be further coupled to a drill or other external tool (not shown) configured to couple to and cause rotation of the driver 1330.

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the disclosed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Although the embodiments of the present disclosure and their advantages have been described in detail, it should be understood that various changes, substitutions and alterations can be made herein without departing from the spirit and scope of the disclosure as defined by the appended claims. Moreover, the scope of the present disclosure is not intended to be limited to the particular embodiments of the process, machine, manufacture, composition of matter, means, methods and steps described herein. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for providing reduction of a bone fracture, the system comprising:
    a screw;
    a driver configured to drive the screw into a bone;
    a retaining sleeve coupled to a first end of the driver, wherein the retaining sleeve is configured to couple to the screw;
    a sleeve comprising a longitudinal bore extending along a length of the sleeve between a first end of the sleeve and a second end of the sleeve, wherein the longitudinal bore is configured to enable the first end of the driver to be inserted through the first end of the sleeve and enable the retaining sleeve to be inserted through the second end of the sleeve, and wherein the longitudinal bore of the sleeve comprises a threaded portion and the driver comprises one or more threads configured to interface with the threaded portion of the longitudinal bore of the sleeve; and
    a locking mechanism configurable into a first state that locks the sleeve to the driver and a second state that unlocks the sleeve from the driver.

2. The system of claim 1, wherein the driver comprises one or more notches, wherein the locking mechanism is integrated with the sleeve, wherein, when the locking mechanism is configured into the first state, the locking mechanism engages the one or more notches of the driver such that rotation of the driver causes simultaneous rotation of the sleeve, and wherein, when the locking mechanism is configured into the second state, the locking mechanism disengages the one or more notches of the driver such that rotation of the driver is independent of rotation of the sleeve.

3. The system of claim 1, wherein the first end of the driver comprises a drive interface, wherein the screw comprises a driver interface, and wherein the retaining sleeve is configured to retain the screw such that the drive interface of the driver mates with the driver interface of the screw.

4. The system of claim 1, wherein, when the locking mechanism is configured into the first state, the retaining sleeve is disposed within the longitudinal bore of the sleeve.

5. The system of claim 1, wherein the screw comprises a first threaded portion, a second threaded portion, and a non-threaded portion separating the first threaded portion and the second threaded portion, the first threaded portion corresponding to a first end of the screw and the second threaded portion corresponding to a second end of the screw.

6. The system of claim 5, wherein, when the locking mechanism is configured into the first state, the retaining sleeve and the second threaded portion are disposed entirely within the longitudinal bore of the sleeve.

7. The system of claim 5, wherein, when the locking mechanism is configured into the first state, the retaining sleeve is disposed entirely within the longitudinal bore of the sleeve, a first portion of the second threaded portion of the screw is disposed within the sleeve, and a second portion of the second threaded portion of the screw is disposed outside the sleeve, wherein the first portion of the second threaded portion of the screw is larger than the second portion of the second threaded portion of the screw.

8. The system of claim 1, wherein a first end of the screw comprises a self-drilling tip having one or more first threads, and a second end of the screw comprises one or more second threads and a groove, and wherein the retaining sleeve comprises one or more retention members configured to couple to the groove of the screw.

9. The system of claim 8, wherein each of the one or more retention members of the retaining sleeve is configured to removably couple to the groove by a compression fit, a snap fit, or both.

10. The system of claim 1, further comprising a resilient member configured to bias the locking mechanism into the first state.

11. The system of claim 1, wherein the driver comprises one or more visual indicators corresponding to one or more operational states, the one or more operational states comprising at least one of:
a first operational state indicating the retaining sleeve is configured to be removably coupled to the screw; and
a second operational state indicating that the screw has been driven into and is flush with a surface of a bone.

12. The system of claim 1, wherein, when the locking mechanism is configured into the first state, the sleeve is configured to retain proximal threads of the screw within the sleeve and to provide a compressive force as distal threads of the screw are driven through a first fragment of the bone and into a second fragment of the bone.

13. The system of claim 12, wherein retaining the proximal threads of the screw within the sleeve as distal threads of the screw are driven through the first fragment of the bone and into the second fragment of the bone delays engagement of the proximal threads and the first fragment of the bone until compression by the sleeve is achieved with respect to the first fragment of the bone and the second fragment of the bone.

14. A system for providing reduction of a bone fracture, the system comprising:
a screw;
a driver configured to drive the screw into a bone;
an inner sleeve comprising a longitudinal bore extending along a length of the inner sleeve between a first end of the inner sleeve and a second end of the inner sleeve, the longitudinal bore of the inner sleeve configured to enable the driver to be inserted through the inner sleeve, wherein the inner sleeve comprises:
a retaining sleeve configured to couple to the screw; and
a compression mechanism configured to provide a compressive force as the screw is driven into the bone;
an outer sleeve comprising a longitudinal bore configured to enable insertion of the inner sleeve through the outer sleeve;
one or more channels, wherein each of the one or more channels comprises a first channel portion and a second channel portion; and
a locking sleeve comprising a longitudinal bore configured to enable insertion of the outer sleeve through the locking sleeve, wherein the locking sleeve comprises one or more pins disposed within the longitudinal bore of the locking sleeve, each of the one or more pins configured to slidably engage a corresponding one of the one or more channels of the inner sleeve, wherein the locking sleeve is configurable into a first state that locks the locking sleeve to the outer sleeve and prevents the retaining sleeve from exiting the outer sleeve, wherein the locking sleeve is configured into the first state when the one or more pins are slidably engaged with the first channel portion of the corresponding ones of the one or more channels of the inner sleeve, wherein the locking sleeve is configurable into a second state that unlocks the outer sleeve from locking sleeve and enables the retaining sleeve to exit the outer sleeve, and wherein the locking sleeve is configured into the second state when the one or more pins are slidably engaged with the second channel portion of the corresponding ones of the one or more channels of the inner sleeve.

15. A system for providing reduction of a bone fracture, the system comprising:
a screw;
a driver configured to drive the screw into a bone, wherein the driver comprises one or more notches;
a retaining sleeve coupled to a first end of the driver, wherein the retaining sleeve is configured to couple to the screw;
a sleeve comprising a longitudinal bore extending along a length of the sleeve between a first end of the sleeve and a second end of the sleeve, wherein the longitudinal bore is configured to enable the first end of the driver to be inserted through the first end of the sleeve and enable the retaining sleeve to be inserted through the second end of the sleeve, and wherein the longitudinal bore of the sleeve comprises a threaded portion and the driver comprises one or more threads configured to interface with the threaded portion of the longitudinal bore of the sleeve;
a locking mechanism configurable into a first state that locks the sleeve to the driver and a second state that unlocks the sleeve from the driver, wherein the locking mechanism is integrated with the sleeve, wherein, when the locking mechanism is configured into the first state, the locking mechanism engages the one or more notches of the driver such that rotation of the driver causes simultaneous rotation of the sleeve, and wherein, when the locking mechanism is configured into the second state, the locking mechanism disengages the one or more notches of the driver such that rotation of the driver is independent of rotation of the sleeve.

16. The system of claim 15, wherein the screw comprises a first threaded portion, a second threaded portion, and a non-threaded portion separating the first threaded portion and the second threaded portion, the first threaded portion corresponding to a first end of the screw and the second threaded portion corresponding to a second end of the screw.

17. The system of claim 15, wherein, when the locking mechanism is configured into the first state, the retaining sleeve is disposed entirely within the longitudinal bore of the sleeve, a first portion of the second threaded portion of the screw is disposed within the sleeve, and a second portion of the second threaded portion of the screw is disposed outside the sleeve, wherein the first portion of the second threaded portion of the screw is larger than the second portion of the second threaded portion of the screw.

18. The system of claim 15, wherein, when the locking mechanism is configured into the first state, the sleeve is configured to retain proximal threads of the screw within the sleeve and to provide a compressive force as distal threads of the screw are driven through a first fragment of the bone and into a second fragment of the bone, wherein retaining the proximal threads of the screw within the sleeve as distal threads of the screw are driven through the first fragment of the bone and into the second fragment of the bone delays engagement of the proximal threads and the first fragment of the bone until compression by the sleeve is achieved with respect to the first fragment of the bone and the second fragment of the bone.

* * * * *